United States Patent [19]

Yokoyama et al.

[11] Patent Number: 4,981,982

[45] Date of Patent: Jan. 1, 1991

[54] CONDENSATION CATALYST AND CATALYTICAL CONDENSATION PROCESS FOR ORGANIC CARBOXYLIC ANHYDRIDES

[76] Inventors: Yoshio Yokoyama, Tokyo, Japan; Kikuko Yokoyama, heir, 6-15, Honamanuma 2-chome, Suginami-ku, Tokyo, Japan

[21] Appl. No.: 526,764

[22] Filed: May 23, 1990

Related U.S. Application Data

[63] Continuation of Ser. No. 241,737, Sep. 8, 1988, abandoned.

[30] Foreign Application Priority Data

Sep. 9, 1987 [JP] Japan .................................. 62-224103

[51] Int. Cl.$^5$ ............................................. C07C 50/18
[52] U.S. Cl. .................................................... 522/208
[58] Field of Search ............................................ 552/208

[56] References Cited

U.S. PATENT DOCUMENTS

| 4,220,597 | 9/1980 | Halcourt et al. | 260/369 |
| 4,379,939 | 4/1983 | Kadel et al. | 552/308 |
| 4,510,087 | 4/1985 | Hattori et al. | 260/371 |
| 4,521,341 | 6/1985 | Kröck et al. | 260/371 |
| 4,666,632 | 5/1987 | Goliaszewski et al. | 260/364 |

FOREIGN PATENT DOCUMENTS

| 2430567 | 1/1976 | Fed. Rep. of Germany . |
| 2442911 | 3/1978 | Fed. Rep. of Germany . |
| 57-38742 | 3/1982 | Japan . |

*Primary Examiner*—Richard L. Raymond
*Assistant Examiner*—Raymond Covington
*Attorney, Agent, or Firm*—Finnegan, Henderson, Farabow, Garrett and Dunner

[57] ABSTRACT

A condensation reaction catalyst useful for producing an organic compound, for example, anthraquinone compounds from phthalic dianhydride and optionally benzene, comprises a catalytic principal component consisting of a solid acid substance, for example, compound oxides or zeolite, and an additional basic component consisting of ammonia or a volatile organic base, for example, isopropylamine, n-butylamine, or pyridine, and attached to at least strong acid sites of the solid acid substance.

7 Claims, No Drawings

CONDENSATION CATALYST AND CATALYTICAL CONDENSATION PROCESS FOR ORGANIC CARBOXYLIC ANHYDRIDES

This application is a continuation of application Ser. No. 07/241,737, filed Sept. 8, 1988, now abandoned.

BACKGROUND OF THE INVENTION (1) Field of the Invention

The present invention relates to a condensation catalyst and a catalytical condensation process in the presence of same. More particularly, the present invention relates to a condensation catalyst and a process for catalytically condensing organic carboxylic anhydrides, for example, phthalic anhydride, in the presence of the condensation catalyst to produce condensation products, for example, anthraquinone at a high yield and purity.

(2) Description of the Related Art

Various methods for producing anthraquinone are known, as follows.

(A) Anthracene is converted to anthraquinone by a catalytic oxidation method. This method is disadvantageous in that it is difficult to obtain a starting material consisting essentially of anthraquinone, and that the starting material contains a carcinogen.

(B) Anthraquinone is produced by a liquid phase Friedel-Crafts reaction of phthalic dianhydride with benzene in the presence of aluminum chloride ($AlCl_3$) to produce o-benzoylbenzoic acid followed by acid cyclization. This method is disadvantageous in that a large amount of aluminum chloride, which is expensive, is consumed, and an excess of benzene is used.

(C) A gas phase Friedel-Crafts reaction method for producing anthraquinone from phthalic dianhydride with benzene was attempted, but a satisfactory catalyst and process for industrial working was not attained.

(D) As disclosed in Japanese Unexamined Patent Publication No. 57-38742 (1982) anthraquinone can be produced from 1,4-naphthoquinone and a small excess of 1,3-butadiene by a Diels-Alder reaction to give tetrahydroanthraquinone, followed by air oxidation in the presence of a base. This method is disadvantageous in that the procedures are complicated and phthalic anhydride is produced as a by-product.

(E) Indane compounds can be converted to corresponding anthraquinone compounds by a catalytical oxidation method. This method is disadvantageous in that the indane compound to be used as a starting material is expensive and harmful substances are produced as by-products.

(F) As disclosed in German Unexamined Patent Publication Nos. 2442911 and 2430567 diphenylmethane compounds can be converted to corresponding anthraquinone compounds by a catalytical oxidation method. This method comprises a plurality of steps and thus a long time is needed to complete the reaction.

(G) U.S. Pat. No. 3,932,474 discloses a process for producing anthraquinone by condensation of benzene with carbon monoxide (CO) in the presence of copper chloride ($CuCl_2$). Namely, in this method, copper chloride must be used in a large amount.

(H) With respect to the liquid phase Friedel-Crafts reaction method for producing anthraquinone from phthalic dianhydride and benzene, U.S. Pat. No. 4,379,092 discloses a new method using a mixture of hydrogen fluoride (HF) and boron trifluoride ($BF_3$) instead of aluminum chloride. Also, U.S. Pat. No. 4,666,532 discloses a new liquid phase Friedel-Crafts reaction method using a solid superstrong acid under pressure.

These methods, however, are disadvantageous in that the process steps are complicated and thus impractical for industrial working.

In view of the above-mentioned various methods for producing anthraquinone, the gas phase Friedel-Crafts reaction method is most preferable if a new catalyst having a high catalytic activity, durability and selectivity is attained, because the starting material is easily obtainable and cheap and the process is simple and can be carried out at a low cost.

Also, the new catalyst and process are obviously useful for the production of not only anthraquinone from phthalic dianhydride, and optionally, benzene, but also other organic compounds from other organic starting compounds.

SUMMARY OF THE INVENTION

An object of the present invention is to provide a condensation catalyst and a catalytical condensation process using same to produce an organic compound, for example, anthraquinone, at a high efficiency.

Another object of the present invention is to provide a condensation catalyst having a high catalytic activity, durability, and selectivity for organic starting compound, and a catalytical condensation process for producing an organic compound, for example, anthraguinone in the presence of the condensation catalyst at a high yield and purity.

The above-mentioned objects can be attained by the condensation catalyst of the present invention, which comprises a catalytic principal component consisting of at least one solid acid substance, and an additional basic component consisting of at least one member selected from the group consisting of ammonia and volatile organic bases and attached to at least strong acid sites of the solid acid substance.

The process of the present invention for catalytically producing an organic compound, comprises the steps of bringing a feed gas containing, as a starting material, at least one organic carboxylic anhydride into contact with a condensation catalyst comprising a catalytic principal component consisting of at least one solid acid substance, and an additional basic component consisting of at least one member selected from the group consisting of ammonia and volatile organic bases and attached to at least strong acid sites of the solid acid substance; and collecting the condensation product.

DESCRIPTION OF THE PREFERRED EMBODIMENTS

The catalyst and catalytical process of the present invention are useful for condensing a starting material comprising not only the organic carboxylic anhydride alone but also the organic carboxylic anhydride with other compounds.

For example, anthraquinone compound can be produced by catalytical condensation of phthalic dianhydride alone or phthalic dianhydride with benzene.

The organic carboxylic anhydrides, to which the catalyst and process of the present invention are effectively applied, include phthalic dianhydride and phthalic dianhydride compounds substituted by a halogen atom, alkyl radical preferably having 1 to 12 carbon atoms, aryl radical, for example, phenyl, 2-methylphenyl, 4-methylphenyl or naphthyl radicals or aralkyl radical, for example, benzyl, phenylethyl, phenylpropyl or phenylbutyl radical.

Also, the other compounds to be condensed with the organic carboxylic anhydride include benzene and benzene compounds substituted with a halogen atom, alkyl radical preferably having 1 to 12 carbon atoms, aryl radical, for example, phenyl, 2-methylphenyl, 4-methylphenyl, or naphthyl radical, aralkyl radical, for example, benzyl, phenylethyl, phenylpropyl or phenylbutyl radical.

In this specification, the catalyst and process of the present invention will be explained by a preferable embodiment of the present invention, in which anthraquinone compounds are produced from corresponding phthalic dianhydride compounds, and optionally, benzene compounds. Note, the present invention is not in any way limited to this preferable embodiment.

The condensation catalyst of the present invention comprises a catalytic principal component and an additional basic component. The catalytic principal component consists of at least one solid acid substance having acid sites. The additional basic component consists of at least one member selected from ammonia and volatile organic bases and is attached to at least strong acid sites of the solid acid substance so as to neutralize the at least strong acid sites.

In the catalyst of the present invention, the solid acid substance is not limited to specific types of substances, but is preferably selected from (1) compound oxides consisting of at least two members selected from oxides of elements of Groups IIA, IIB, IIIA, IIIB, IVA and IVB of the periodic table, vanadium, chromium, manganese, iron, cobalt, nickel, copper, molybdenum, tungsten, and rare earth elements;

(2) sintered solid acids comprising a sintering product of a substrate component consisting of at least one member selected from oxides and compound oxides of the above-mentioned elements and diatomaceous earth and associated with an additional acid component consisting of at least one member selected from phosphoric acid and sulfuric acid;

(3) solid acids comprising a substrate component consisting of at least one member selected from oxides and compound oxides of the above-mentioned elements and diatomaceous earth and associated with an additional salt component consisting of at least one member selected from metal phosphates and metal sulfates;

(4) heteropolyacids selected from silicotungstic acid and phosphotungstic acid combined with silica gel;

(5) Crystalline zeolite of the empirical formula:

$$M_{x/n}[(AlO_2)_x(SiO_2)_y]\cdot wH_2O$$

wherein M represents a cation selected from hydrogen, elements of groups IA, IB, IIA, IIB, IIIA and IIIB of the Periodic Table, transition elements and rare earth elements, n represents a valence of the cation M, x and y respectively represent the number of group ($AlO_2$) and group ($SiO_2$) per crystal until cell and w represents the number of water molecules per crystal unit cell.

The oxides can be produced by roasting hydroxides, carbonates and other thermally decomposable salts of the above-mentioned elements. The composite oxides (1) can be produced by conventional co-precipitation, kneading or impregnating procedures from the corresponding compounds of the above-mentioned elements, and conventional drying and roasting procedures.

Also, the sintered solid acids (2) can be produced by associating a substrate component consisting of at least one member selected from the above-mentioned compound elements and diatomaceous earth with an additional acid component consisting of at least one member selected from phosphoric acid and sulfuric acid and sintering the acid-associated substrate at a temperature of 200° C. to 500° C.

The solid acid (3) can be produced by associating a substrate component consisting of at least one member selected from oxides and compound oxides of the above-specified elements and diatomaceous earth with an additional salt component consisting of at least one member selected from metal phosphate and metal sulfates, for example, phosphates and sulfates of Fe, Al, Cr, Cu, Zn, Co, Cd, Ni and Mn.

The usual crystalline zeolite contains sodium (Na) as a cation M in the above-mentioned empirical formula. The Na ion ($Na^+$) is ion-exchanged with hydrogen ions ($H^+$) or other metal ions, and the resultant zeolite is combined with a matrix, for example, silica-alumina, clay or kaolin. The resultant combination is molded into a predetermined shape and dimensions to provide a catalyst.

The heteropolyacid (5) consists of at least one member selected from silicotungstic acid and phosphotungstic acid combined with silica gel.

The catalytic principal component is molded into a predetermined shape and dimensions, for example, beads, pellets, grains or particles having a size of 0.01 to 10 mm.

In the condensation catalyst of the present invention, the additional basic component consists of at least one member selected from ammonia and volatile organic bases.

The additional basic component should be chemically stable at a temperature at which the catalyst is used for a condensation process, for example, 240° C. to 500° C., over a long period of time.

Preferably, the organic bases have a boiling point of 20° C. to 240° C., more preferably 20° C. to 120° C., and the selected from aliphatic amines, for example, diethylamine, triethylamine, n-propylamine, isopropylamine, diisopropylamine, allylamine, n-butylamine, isobutylamine, sec-butylamine, tert-butylamine, and dimethylbutylamine; aromatic amines, for example, aniline; pyridine, picoline and quinoline. The most: preferable bases are ammonia, isopropylamine and n-butylamine.

In the condensation catalyst of the present invention, the additional basic component is attached to at least strong acid sites of the solid acid substance of the catalytic principal component to neutralize at least the strong acid sites of the solid acid substance.

In the preparation of the catalyst, weak acid sites and mild acid sites of the solid acid substance may be associated with the additional basic component.

When the catalyst is heated for the condensation reaction, for example, at a temperature of 240° C. or more, the additional basic component associated with the weak and mild acid sites of the solid acid substance are easily dissociated from these acid sites, and only the association of the strong acid sites with the additional basic component can be maintained.

Accordingly, the condensation catalyst of the present invention exhibits an excellent acidic property, i.e., a mild acid strength, and a high adicity, and thus is very useful for condensing a starting material containing an organic carboxylic anhydride, and optionally, other organic compound at a very high efficiency. If the catalyst has an excessively high acid strength, for example, when the strong acid sites are not neutralized, undesirable side reactions and decomposition of the starting compound and the resultant product occur during the condensation reaction. Therefore, this type of catalyst exhibits a decreased selectivity and results in a reduction of the yield of the condensation product. Also, the durability of the catalyst is affected by by-products, for example, coke.

The condensation catalyst can be produced by bringing the additional basic component in the gas or liquid phase into contact with the catalyst principal component so that the additional basic compound is absorbed on at least the strong acid sites of the catalyst principal component. When the catalytic principal component is finely porous, the additional basic component in gas or liquid phase should be diffusable into the fine pores so as to be absorbed on the inside surfaces of the pores.

When the condensation catalyst is produced in a liquid phase, the catalytic principal component is immersed in an neutral organic solvent in the presence of a Hammett indicator corresponding to an acid strength necessary for the condensation catalyst, and a solution of the additional basic component is added to the solvent to allow the additional basic component to be selectively absorbed on the strong acid sites of the catalytic principal component.

The condensation catalyst of the present invention may be prepared before application to the condensation process. Otherwise, the condensation catalyst may be prepared and maintained during the condensation process in such a manner that the catalytic principal component is placed in the condensation reaction system and a feed gas containing the starting material to be condensed and the additional basic component is fed into the condensation reaction system, to allow the additional basic component to be absorbed by the catalytic principal component and form a condensation catalyst of the present invention.

The amount of the additional basic component to be attached to the catalytic principal component can be determined in consideration of the structure, composition and acidic property of the catalytic principal component.

In the process of the present invention, a feed gas containing, as a starting material to be condensed, at least one organic carboxylic anhydride compound, for example, phthalic dianhydride alone or a mixture of phthalic dianhydride with benzene, is brought into contact with the specific condensation catalyst of the present invention at a temperature of 240° C. to 450° C.

In the condensation reaction system, the amount of the starting material to be fed to the condensation catalyst is preferably in the range of from 0.5 to 8.0 by WHSV (weight hourly space velocity) based on the weight of the catalyst. The reaction can be carried out under a reduced pressure, ambient atmospheric pressure or increased pressure in a fixed bed, moving bed or fluidized bed reaction apparatus.

The condensation process of the present invention can be carried out in the presence of a promoter consisting of at least one member selected from proton donors, protonic acids, and electron donors having at least one member selected from oxygen, sulfur, nitrogen, and halogen atoms and capable of forming cations other than proton.

The promoter is preferably selected from water; alcohols, for example, tert-butanol and benzyl alcohol; organic carboxylic acids, for example, henzoic acid; aldehydes, for example, henzaldehyde; carbon dioxide, air, perchloromethane ($CCl_4$); and halogenated hydrocarbons, for example, benzylchloride and p-chlorotoluene.

The promoter is preferably used in an amount of 0.01% to 10% based on the amount of the starting material.

The condensation catalyst can be continuously used over a long period of time, and this is a great advantage of the present invention. But, if the catalyst is deactivated by a deposit of the by-product coke, the catalyst can be revived and re-activated by burning the coke with a hot air at a temperature of 450 to 500° C. for 40 to 60 minutes.

When the condensation reaction is completed, the resultant condensation product is collected by an ordinary method, for example, by cooling, and non-reacted starting material is recovered.

The feed gas may contain a carrier gas comprising, for example, carbon dioxide and nitrogen. Usually, the feed gas contains the starting material in a content of 5% by volume or more.

The condensation catalyst and process of the present invention is advantageously applied to the catalytical production of an anthraquinone compound from a phthalic dianhydride compound or a mixture of a phthalic dianhydride and a benzene compound.

For example, in the process of the present invention, a feed gas containing at least one member selected from (a) phthalic anhydride compounds of the formula (I) and (b) mixtures of benzene compounds of the formula (II) and the phthalic anhydride compounds of the formula (I):

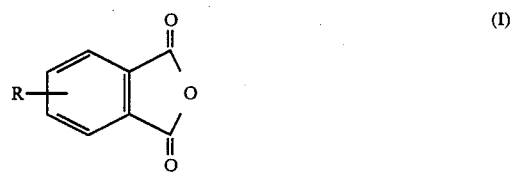

(I)

(II)

wherein R represents a member selected from the group consisting of hydrogen and halogen atoms and alkyl, aryl and aralykyl radicals, is brought into contact with the condensation catalyst at a temperature of 240° C. to 450° C., to produce an anthraquinone compound of the formula (III):

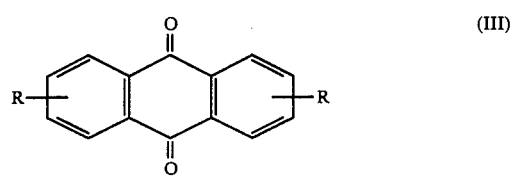

(III)

wherein R is as defined above.

In the formulae (I) (II) and (III), R preferably represents hydrogen, chlorine, bromine and fluorine atoms, alkyl radicals having 1 to 12 carbon atoms, for example, methyl, ethyl, propyl butyl and pentyl benzyl and phenyl radicals.

When the mixture of the phthalic anhydride compound and the benzene compound is used, preferably the benzene compound is used in an excessive amount. Usually, the mixing ratio of the phthalic anhydride compound to the benzene compound is in the range of from 1:2 to 1:20.

After the completion of the condensation step, the resultant anthraquinone compound, is collected and non-reacted phthalic anhydride compound and benzene compound are recovered.

For example, in accordance with the method disclosed in Japanese Unexamined Patent Publication No. 57-38743 (1982), a resultant condensation reaction mixture is cooled to allow the anthraquinone compound to be dissolved or suspended in non-reacted phthalic anhydride compound in a liquid state, the solution or slurry is separated from non-reacted benzene compound which is still in the gas phase and easily recovered, the phthalic anhydride compound is recovered by distillation, and the anthraquinone compound is collected as a distillation residue. Also, water vapor in the reaction mixture can be removed by using a moisture absorber.

The recovered phthalic anhydride compound and benzene compound are returned to the condensation reaction system.

The condensation catalyst of the present invention is characteristic in that the strong acid sites of the solid acid substance are selectively neutralized with a basic compound at a high stability at the condensation reaction temperature. Even where the weak acid sites and mild acid sites of the solid acid substance are neutralized with the specific basic compound of the present invention at a lower temperature than the condensation reaction temperature, these acid sites can be released from the basic compound at the condensation reaction temperature and the resultant catalyst can exhibit an appropriate acidic property, i.e., a mild acid strength and a high acidity, and promote the condensation reaction at a very high efficiency.

The present invention allows conventional solid acid substances which have strong acid sites and thus which can not be practically utilized as a condensation catalyst, to be utilized as a catalytic principal component of the condensation catalyst.

The present invention will be illustrated in detail by the following examples which are representative and in no way restrict the scope of the present invention.

EXAMPLE 1 AND COMPARATIVE EXAMPLE 1

In Example 1, a catalytic principal component consisting of a compound oxide was produced in the following manner.

An aqueous solution of a mixture of ethyl orthosilicate and titanium tetrachloride was added with an aqueous solution of ammonia to provide a mixture of hydroxides of silicon and titanium.

Separately, an aqueous solution of magnesium chloride was mixed with a aqueous solution of ammonia to provide magnesium hydroxide.

The mixture of hydroxides of silicon and titanium was admixed with the magnesium hydroxide at a mixing ratio of 1:1:1 in terms of $TiO_2$, $SiO_2$, and MgO. The admixture was washed with water to an extent such that no residual metal ion was detected, evenly stirred and kneaded, and then shaped into beads. The resultant beads were dried at a temperature of 100° C. and heated at a temperature of 500° C. for 3 hours. The resultant beads of a catalytic principal component consisting of $TiO_2$ - $SiO_2$ - MgO compound oxide had a size of from 4 to 6 mm.

A stainless steel reaction tube having a diameter of 27 mm was charged with 60 g of the beads and the beads were externally heated at a temperature of 380° C.

A feed gas containing a mixture of one molar part of phthalic dianhydride with 10 molar parts of benzene in an amount of 3.2 by WHSV based on the weight of the catalyst and 1% by weight of ammonia which were diluted by 15 Nl/hour of nitrogen gas, flowed through the reaction tube for 12 hours.

The conversion of phthalic dianhydride was 34%, and the yield of anthraquinone was 92%. The resultant anthraquinone powder had a pale yellow color and a degree of purity of 98% or more.

The catalyst beads were removed from the reaction tube after the reaction tube was cooled, and it was found that the beads had a grayish black color and still retained a sufficient catalytic activity for actual use.

The catalyst beads were burnt in air at a temperature of 480° C. for 40 minutes, for reactivation thereof.

The reactivated catalyst beads exhibited substantially the same catalytic activity as non-used beads.

In comparative Example 1, the same procedures as those described in Example 1 were carried out, except that the feed gas did not contain ammonia.

A yellowish orange Anthraquinone powder having a degree of purity of 78% was obtained at a conversion of 55% and a yield of 34%.

EXAMPLE 2 AND COMPARATIVE EXAMPLE 2

In Example 2, a zeolite having a composition of:

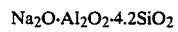

$Na_2O \cdot Al_2O_2 \cdot 4.2SiO_2$ was ion-exchanged so that 30% of Na ions were replaced by rare earth metal ions consisting of 3% of La ions, 92% of Ce ions, and 5% of Nd ions, and hydrogen ions ($H^+$). The ion-exchanged zeolite contained 0.5% by weight of $Na_2O$.

The ion-exchanged zeolite in an amount of 70 parts by weight was mixed with 30 parts by weight of a matrix consisting of aluminosilicate having a ratio of $Al_2O_3$ to $SiO_2$ of 98:2. The mixture was shaped into beads having a size of 4 to 6 mm by an ordinary beads-forming method.

The same reaction tube as mentioned in Example 1 was charged with 60 g of the resultant zeolite-containing beads, and the beads were heated at a temperature of 200° C.

A gas containing 1% of water vapor, 3% of ammonia diluted with 25 Nl/hour of carbon dioxide was made to flow through the reaction tube for one hour, to provide catalyst beads.

The catalyst beads were then heated at 350° C. and a feed gas containing a mixture of 1 molar part of phthalic dianhydride and 9 molar parts of benzene diluted with 10 Nl/hour of carbon dioxide gas made of flow through the reaction tube. The total amount of the phthalic dianhydride-benzene mixture was 1.5 by WHSV based on the weight of the catalyst.

After an initial induction period of about 1.5 hours, the condensation procedure was continued for 12 hours.

At 6 hours after the start of the condensation procedure, a gas containing 1% of water vapor and 2% of ammonia diluted by 10 Nl/h of carbon dioxide gas was introduced into the reaction tube for 6 hours.

A anthraquinone powder having a pale yellow color and a degree of purity of 98% was obtained at a conversion of 38% and a yield of 96%.

The residual catalyst beads were reactivated in the same manner as mentioned in Example 1.

The reactivated catalyst beads exhibited the same catalytic activity as non-used beads.

In Comparative Example 2, the same procedures as those described in Example 2 were carried out, except that the ammonia-absorbing operation for the catalyst principal component pellets was omitted.

A yellowish brown anthraquinone powder having a degree of purity of 71% was obtained at a conversion of 66% and a yield of 30%.

EXAMPLE 3 AND COMPARATIVE EXAMPLE 3

In the Example 3, the same procedures as those described in Example 2 were carried out with the following exception.

A zeolite having a composition of $$Na_2O_1 \cdot Al_2O_3 \cdot 2.5SiO_2$$

was ion-exchanged so that 50% of Na ions were exchanged by rare earth metal ions consisting of 5% of La ions and 95% of Ce ions, and hydrogen ions. The ion-exchanged zeolite contained 0.8% by weight of $Na_2O$.

The condensation reaction was carried out at a temperature of 340° C. by introducing a feed gas containing a mixture of 1 molar part of phthalic dianhydride and 10 molar parts of benzene diluted with 10 Nl/h of carbon dioxide gas. The total amount of the phthalic dianhydride-benzene mixture was 1.3 by WHSV based on the weight of the catalyst.

A pale yellow anthraquinone powder having a degree of purity of 98% was obtained at a conversion of 36% and a yield of 95%.

The residual beads were reactivated by the same procedure as mentioned in Example 1.

In Comparative Example 3, the same procedures as in Example 3 were carried out, <except that the catalyst principal component beads were not neutralized with ammonia.

A yellowish orange anthraquinone powder having a degree of purity of 73% was obtained at a conversion of 58% and a yield of 28%.

EXAMPLE 4 AND COMPARATIVE EXAMPLE 4

In Example 4, the same procedures as those described in Example 3 were carried out with the following exception.

The starting mixture consisted of 1 molar part of phthalic anhydride and 8 molar parts of toluene and was used in an amount of 1.5 by WHSV based on the weight of the catalyst. The condensation reaction was carried out at a temperature of 345° C.

A pale yellow 2-methyl anthraquinone powder having a degree of purity of 97.6% was obtained at a conversion of 40% and a yield of 93%.

The used catalyst beads were reactivated by the same manner as mentioned in Example 1.

In Comparative Example 4, the same procedures as in Example 4 were carried out, except that the catalytic principal component beads were not neutralized with ammonia.

A dark yellow 2-methyl anthraquinone powder having a degree of purity of 76% was obtained at a conversion of 58% and a yield of 32%.

EXAMPLE 5 AND COMPARATIVE EXAMPLE 5

In Example 5, the same procedures as those described in Example 3 were carried out, with the following exception.

A zeolite having the composition $$Na_2O \cdot Al_2O_3 \cdot 4.2SiO_2$$

was ion-exchanged so that 8% by Na ions were exchanged by La ions and H ions. The ion-exchanged zeolite contained 1.9% by weight of $Na_2O$.

The ammonia-attached catalyst beads were prepared from the ion-exchanged zeolite in the same manner as mentioned in Example 3.

The reaction tube was charged with 60 g of the catalyst beads and a feed gas consisting of 40% of phthalic dianhydride and 60% of carbon dioxide was made to flow through the reaction tube at a temperature of 350° C. for 12 hours. The amount of phthalic dianhydride was 2.4 by WHSV based on the weight of the catalyst.

A pale yellow anthraquinone powder having a degree of purity of 98% was obtained at a conversion of 38% and a yield of 97%.

The used catalyst beads was reactivated by the same procedure as mentioned in Example 1.

In Comparative Example 5, the same procedures as those described in Example 5 were carried out, except that the zeolite-containing catalytic principal component beads were not neutralized with ammonia.

A dark yellow anthraquinone having a degree of purity of 77% was obtained at a conversion of 62% and a yield of 38%.

EXAMPLE 6 AND COMPARATIVE EXAMPLE 6

In Example 6, a catalytic principal component was prepared by impregnating substrate beads consisting of 40% by weight of $Al_2O_3$ and 60% by weight of $SiO_2$ and having a size of 4 to 6 mm with 1.0% by weight of $Fe_2(SO_4)_3$ and 8.0% by weight of $Al_2(SO_4)_3$, drying the resultant catalytic principal component beads at 100° C. for 12 hours, firing the beads at a temperature of 450° C. for 6 hours, and cooling them under vacuum.

The catalytic principal component beads were immersed in dehydrated benzene, and neutralized with a 1/10N solution of isopropylamine in benzene in the presence of a Hammett indicator consisting of dicinnamalacetone.

The isopropylamine-attached beads were separated from benzene by filtration and dried.

The same condensation procedures as those described in Example 1 were carried out, except that the above-mentioned catalyst beads were used at a temperature of 380° C.

A pale yellow anthraquinone powder having a degree of purity of 97% was obtained at a conversion of 12% and a yield of 97%.

In Comparative Example 6, the same procedures were used as those described in E<ample 6, except that the catalyst principal component beads were not neutralized with isopropylamine.

A light yellowish orange anthraquinone powder having a degree of purity of 87% was obtained at a conversion of 23% and a yield of 62%.

EXAMPLE 7 AND COMPARATIVE EXAMPLE 7

In Example 7, a compound oxide consisting of 10 molar parts of $TiO_2$, 10 molar parts of $SiO_2$, and 1 molar part of MgO was shaped into beads having a size of 4 to 6 mm. The beads was impregnated with 3% by weight of phosphoric acid, and then reacted at a temperature of 400° C. for 4 hours to provide catalytic principal component beads.

The catalytic principal component beads were neutralized with n-butylamine in benzene in the presence of a Hammett indicator consisting of dicinnamalacetone, and then dried to provide catalyst beads.

The same procedures as those described in Example 1 were carried out, except that the above-mentioned catalyst beads were used and the feed gas did not contain ammonia.

A pale yellow anthraquinone powder having a degree of purity of 97.6% was obtained at a conversion of 18% and a yield of 96%.

In Comparative Example 7, the same procedures as those described in Example 7 were carried out, except that the catalytic principal component beads were not neutralized with n-butylamine.

A yellow brown anthraquinone powder having a degree of purity of 64% was obtained at a conversion of 45% and a yield of 28%.

In view of Examples 1 to 7, it is clear that the specific condensation catalyst of the present invention is very effective for producing a condensation product having a very high purity at a very high yield.

In view of Comparative Examples 1 to 7, it is clear that lack of the additional basic component in the condensation catalyst results in a low purity and a very poor yield of the condensation product, even where a conversion of the starting material is relatively high. Also, in each of Comparative Examples 1 to 7, it was found that the catalyst activity of the comparative catalyst decreased 4 to 6 hours after the start of the condensation procedures. Also, after the condensation procedure was completed and the comparative catalyst beads were cooled, it was found that dark black coke was deposited on the surface and in the inside pores of the used comparative catalyst beads, and it was very difficult to reactivate these used comparative catalyst beads.

I claim:

1. A process for producing anthroquinone compounds, comprising catalytically condensing at least one phthalic anhydride compound of the formula (I) with at least one benzene compound of the formula (II):

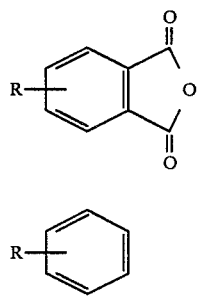

wherein R represents a member selected from the group consisting of hydrogen and halogen atoms and alkyl, aryl and aralkyl radicals, by contacting a feed gas containing, as starting materials, the phthalic anhydride compound and the benzene compound under condensation reaction conditions with a condensation catalyst comprising:

(A) a catalytic principal component consisting of at least one solid acid substance selected from the group consisting of
  (1) compound oxides consisting of at least two members selected from the group consisting of oxides of elements of Groups IIA, IIB, IIIA, IIIB, IVA, and IVB of the periodic table, vanadium, chromium, manganese, iron, cobalt nickel, copper, molybdenum, tungsten and rare earth elements;
  (2) sintered solid acids comprising a sintering product of a substrate component consisting of at least one member selected from the group consisting of oxides and compound oxides of the above-mentioned elements and diatomaceous earth and associated with an additional acid component consisting of at least one member selected from the group consisting of phosphoric acid and sulfuric acid;
  (3) solid acids comprising a substrate component consisting of at least one member selected from the group consisting of oxides and compound oxides of the above-mentioned elements and diatomaceous earth and associated with an additional salt component consisting of at least one member selected from the group consisting of metal phosphates and metal sulfates;
  (4) heteropolyacids selected from the group consisting of silicotungstic acid and phosphotungstic acid combined with slica gel; and
  (5) Crystalline zeolites of the empirical formula:

$$M_{x/n}[(Al_2O_3)_x(SiO_2)_y]\cdot wH_2O$$

wherein M represents a cation selected from the group consisting of hydrogen, atom, elements of groups IA, IB, IIA, IIB, IIIA, IIIB of the Periodic Table, transition elements and rare earth elements, n represents a valence of the cation M, x and y respectively represent the number of group ($Al_2O_3$) and group ($SiO_2$) per crystal unit cell, and w represents the number of water molecules per crystal unit cell; and (B) an additional basic component consisting of at least one member selected from the group consisting of ammonia and volatile organic bases and attached to at least strong acid sites of at least one solid acid substance; and collecting the resulting anthroquinone compound of the formula (III):

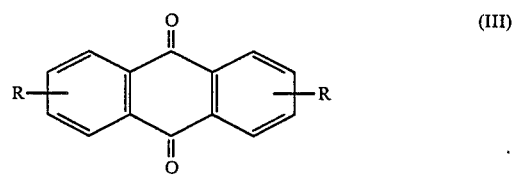

wherein R is as defined above.

2. The process as claimed in claim 1, wherein the feed gas contains the additional basic component in addition to the starting material, and when the feed gas comes into contact with the catalytic principal component, at least the strong acid sites thereof are neutralized by the additional basic component, to form the condensation catalyst.

3. The process as claimed in claim 1, wherein the feed gas is placed in contact with the condensation catalyst in the presence of a promoter consisting of at least one member selected from the group consisting of proton donors, proton acids and electron donors having at least one member selected from the group consisting of oxygen, sulfur, nitrogen and halogen atoms and capable of forming cations other than proton.

4. The process as claimed in claim 1, wherein the feed gas contains a carrier gas consisting of at least one member selected from the group consisting of carbon dioxide and nitrogen.

5. The process as claimed in claim 1, wherein the solid acid substance is selected from the group consisting of:
(1) compound oxides consisting of at least two members selected from the group consisting of oxides of elements of Groups IIA, IIB, IIIA, IIIB, IVA and IVB of the Periodic Table, vanadium, chromium, manganese, iron, cobalt, nickel, copper, molybdenum, tungsten and rare earth elements;
(2) sintered solid acids comprising a sintering product of a substrate component consisting of at least one member selected from the group consisting of oxides and compound oxides of the above-mentioned elements and diatomaceous earth and associated with an additional acid component consisting of at least one member selected from the group consisting of phosphoric acid and sulfuric acid;
(3) solid acids comprising a substrate component consisting of at least one member selected from the group consisting of oxides and compound oxides of the above-mentioned elements and diatomaceous earth and associated with an additional salt component consisting of at least one member selected from the group consisting of metal phosphates and metal sulfates;
(4) heteropolyacids selected from the group consisting of silicotungstic acid and phosphotungstic acid combined with silica gel; and
(5) crystalline zeolite of the empirical formula:

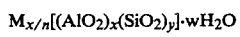

$$M_{x/n}[(AlO_2)_x(SiO_2)_y] \cdot wH_2O$$

wherein M represents a cation selected from the group consisting of hydrogen, atom, elements of groups IA, IB, IIA, IIB, IIIA, IIIB of the Periodic Table, transition elements and rare earth elements, n represents a valence of the cation M, x and y respectively represent the number of group (Al$_2$O$_3$) and group (SiO$_2$) per crystal unit cell, and w represents the number of water molecules per crystal unit cell.

6. The process as claimed in claim 1, wherein the volatile organic base is selected from the group consisting of volatile aliphatic amines, aromatic amines, pyridine, picoline and quinoline.

7. The process as claimed in claim 1, wherein the catalytic condensation reaction conditions include contacting said starting material with said catalyst at a temperature of from 240° C. to 450° C. and a weight hourly space velocity in the range of from 0.5 to 8.0 parts of said starting material to said catalyst, based on said catalyst.

* * * * *

UNITED STATES PATENT AND TRADEMARK OFFICE
CERTIFICATE OF CORRECTION

PATENT NO. : 4,981,982

DATED : January 1, 1991

INVENTOR(S) : Yoshio Yokoyama, Kikuko Yokoyama, heir

It is certified that error appears in the above-identified patent and that said Letters Patent is hereby corrected as shown below:

Column 9, line 26, change "$Na_2O_1$" to --$Na_2O$--.

Signed and Sealed this

Fourth Day of August, 1992

*Attest:*

DOUGLAS B. COMER

*Attesting Officer* — *Acting Commissioner of Patents and Trademarks*